United States Patent [19]
Knaak et al.

[11] Patent Number: 5,981,793
[45] Date of Patent: Nov. 9, 1999

[54] SLIGHTLY WATER-SOLUBLE METAL SALTS, A PROCESS FOR THE PREPARATION THEREOF, AND THE USE THEREOF AS GLOSS ADDITIVES IN THE ELECTROLYTIC DEPOSITION OF METALS

[75] Inventors: Eberhard Knaak, Langenfeld; Joachim Heyer, Neunkirchen-Seelscheid; Marlies Kleinfeld, Wuppertal; Christel Van Wijngaarden, Solingen, all of Germany

[73] Assignee: Blasberg Oberflachentechnik GmbH, Solingen, Germany

[21] Appl. No.: 09/142,857

[22] PCT Filed: Mar. 20, 1997

[86] PCT No.: PCT/EP97/01389

§ 371 Date: Sep. 16, 1998

§ 102(e) Date: Sep. 16, 1998

[87] PCT Pub. No.: WO97/35840

PCT Pub. Date: Oct. 2, 1997

[30] Foreign Application Priority Data

Mar. 23, 1996 [DE] Germany .............. 196 11 565

[51] Int. Cl.$^6$ ................................. C07C 51/305
[52] U.S. Cl. ............................... 562/26; 205/65
[58] Field of Search .................. 562/26; 205/65

[56] References Cited

U.S. PATENT DOCUMENTS

| | | |
|---|---|---|
| 1,788,632 | 1/1931 | Powers . |
| 2,666,738 | 1/1954 | Kardos . |
| 4,455,262 | 6/1984 | Detienne . |

FOREIGN PATENT DOCUMENTS

| | | |
|---|---|---|
| 885 036 | 7/1953 | Germany . |
| 27 31 595 A1 | 1/1979 | Germany . |

OTHER PUBLICATIONS

Thuillier et al., *Préesentés a La Société Chimique*, "Composés organiques sulfurés (*).V. —Condensation du sulfure de carbone et de l'acétone", No. 367, pp. 2182–2186.

Thuillier et al., *Préesentés a La Société Chimique*, "Composés organiques sulfurés (*).VI—Condensation du dulfure de carbone et des cétones aliphatiques", pp. 2187–2193.

*Primary Examiner*—Gary Geist
*Assistant Examiner*—Jean Vollano
*Attorney, Agent, or Firm*—Jacobson, Price, Holman & Stern, PLLC

[57] ABSTRACT

The slightly water-soluble metal salts having the formula I

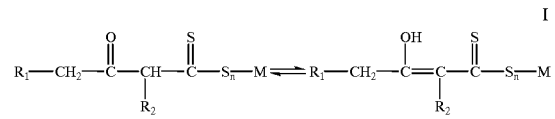

wherein $R_1$ and $R_2$ are the same or different and represent hydrogen or a lower alkyl group of from 1 to 3 carbon atoms, M is the cation of a metal which forms slightly water-soluble sulfides, and n means 1 or 2, and mixtures thereof are prepared by reacting carbon disulfide with ketones having the formula II:

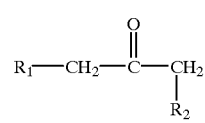

optionally with the addition of non-aqueous inert solvents, in the presence of strong alkali, preferably potassium hydroxide, followed by precipitation of the slightly water-soluble metal salts of formula I by the addition of aqueous solutions of metal salts of the metals M. They are used as gloss additives to electrolytic baths.

5 Claims, No Drawings

SLIGHTLY WATER-SOLUBLE METAL SALTS, A PROCESS FOR THE PREPARATION THEREOF, AND THE USE THEREOF AS GLOSS ADDITIVES IN THE ELECTROLYTIC DEPOSITION OF METALS

This application is the national stage of PCT/EP97/01389 filed Mar. 20, 1997.

The present invention pertains to slightly water-soluble metal salts having the formula I

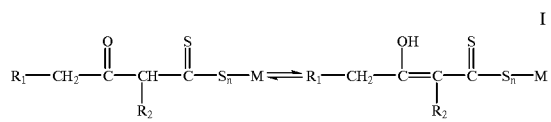

wherein $R_1$ and $R_2$ are the same or different and represent hydrogen or a lower alkyl group of from 1 to 3 carbon atoms, M is the cation of a metal which forms slightly water-soluble sulfides, and n means 1 or 2, and mixtures thereof, a process for the preparation thereof, and the use thereof as gloss additives in the electrolytic deposition of metals.

From DE-PS-885 036, a process is known for the production of shining silver precipitates wherein sulfur-containing compounds, such as carbon disulfide (and other sulfur-containing compounds), are reacted with ketones and strong alkali, followed by acidification, precipitation and, optionally after redissolution with alkali and renewed precipitation with mineral acid, using them as additives for silver plating baths. Frequently, formaldehyde or Turkey red oil were also added to such silver plating baths.

From DE-PS 27 31 595, it is known that such baths can be improved if the condensation products of ketone, alkali hydroxide and carbon disulfide are admixed with water-soluble salts of naphthalenesulfonic acid/formaldehyde condensation products. Especially when added to cyanide-type silver plating baths, it is possible to thus prepare high-gloss silver precipitates.

From the works by Apitzsch, Berichte 37, 1599 (1904), and Berichte 38, 2888 (1905), as well as Berichte 41, 4028 (1908), it has been known that the condensation of ketones with carbon disulfide followed by acidification yields cyclic compounds having the formula:

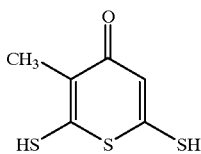

To date, it has been considered that such cyclic compounds accounted for gloss generation in silver plating baths. Mass spectroscopical examinations of such reaction mixtures have now confirmed that the cyclic compounds actually form. In the past, it has been attempted to enrich this cyclic fraction in particular, to add it to the brighteners.

Intensive studies by Applicant have now yielded the surprising result that it is not these cyclic compounds which account for gloss formation, but the compounds of formula I formed as side-products prior to the acidification, wherein, however, M is the cation of a metal which forms sulfides readily soluble in water. In all methods for the preparation of condensation products of ketones with carbon disulfide described and practised to date, there were formed either the water-soluble alkali metal salts, or the slightly soluble cyclic compounds which can be precipitated with acids.

It has now further been established that these side-products, the compounds according to the invention, can be stabilized and separated in an undecomposed form if they are precipitated as slightly water-soluble salts. Slightly soluble salts are predominantly formed by the metals which also form slightly water-soluble sulfides. Thus, in addition to silver, these are in particular copper, lead, bismuth, antimony, cobalt, iron, zinc, palladium, molybdenum, tin, and gold.

It has further been established that these slightly soluble metal salts are not only essentially more stable than the side-products or cyclic compounds, which have been observed to be unstable, but that these slightly soluble metal salts are in addition excellently suited for acting as gloss additives. The usual primary brighteners, such as Turkey red oil and the condensation products of formaldehyde with naphthalenesulfonic acids, can even be dispensed with. At any rate, significantly improved gloss layers of silver are obtained with or without the addition of these known primary brighteners. It appears that these slightly soluble metal salts are capable of redissolving in electrolytes to such an extent that they can serve the function of a brightener.

The novel metal salts are effective in concentrations of 0.005 to 0.3 g/l already. Evidently, the other components of the electrolytes increase the solubility of the slightly soluble metal salts so that they become redissolved. The process for the preparation of the slightly soluble metal salts of formula I is characterized in that carbon disulfide is reacted with ketones having the formula II:

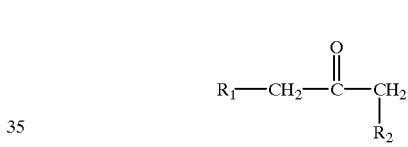

wherein $R_1$ and $R_2$ have the same meaning as above, optionally with the addition of non-aqueous inert solvents, in the presence of strong alkali, preferably potassium hydroxide, followed by precipitation of the slightly water-soluble metal salts of formula I by the addition of aqueous solutions of metal salts of the metals M.

The molar ratio between carbon disulfide and the ketones is not critical. A sufficient amount of alkali hydroxide is always important. The precipitation of the slightly soluble metal salts is also unproblematic since it is sufficient to mix the water-soluble metal salts in an aqueous solution with the reaction mixture. The quantity ratios and process conditions seem to have a certain influence on the quantity ratios of the substances in which n=1 and n=2, respectively. Mostly, both substances are obtained together. The slightly water-soluble metal salts of formula I precipitate and can be separated in the usual way. If desired, they may be washed and dried, and, in this form, also be stored and used later.

It is also possible to use the raw precipitates as additives to gloss electrolytes without further purification and drying since the slightly soluble metal salts of formula I are sufficiently stable in this form as well.

In the following examples, the salts and their preparations are explained in more detail.

EXAMPLE 1

One mole of methyl ethyl ketone is refluxed with 0.65 moles of carbon disulfide and 1.35 moles of potassium hydroxide whereby the reaction temperature is brought to about the boiling point of carbon disulfide. After about 2 to 3 hours of reaction, the reaction mixture is cooled, the supernatant liquid phase is separated from the solid, and the slightly soluble silver salt is precipitated from this liquid phase with a silver salt aqueous solution. It may be washed and dried. The precipitate may also be redissolved immediately in 1% cyanide solution and added as a brightener to a silver electrolyte. When used as an additive to the gloss electrolyte, from 0.05 to 0.3 g/l of this silver salt is sufficient.

EXAMPLE 2

One mole of acetone is reacted with 0.65 moles of carbon disulfide and 1.35 moles of potassium hydroxide. As in example 1, the slightly soluble silver salt is separated from the liquid phase with 20 ml of silver nitrate solution (1 M). It is added to a silver gloss electrolyte which contains from 0.1 to 1 g/l of the silver salt, and 10 ml/l of a formaldehyde/ naphthalenesulfonic acid condensation product as the primary brightener.

EXAMPLE 3

One mole of methyl ethyl ketone, 0.65 moles of carbon disulfide and 1.35 moles of potassium hydroxide are reacted with one another. The liquid phase is precipitated with 25 ml of silver nitrate solution. The precipitate is added in amounts of 0.01 g/l to a gloss electrolyte which contains 1 ml/l of formaldehyde/ naphthalenesulfonic acid condensation product as the primary brightener.

EXAMPLE 4

In a way analogous to that described in example 3, a silver gloss electrolyte is prepared to which 10 ml/l of Turkey red oil is added.

EXAMPLE 5

0.15 moles of methyl ethyl ketone is reacted with 0.6 moles of carbon disulfide and 0.6 moles of KOH. The silver salt is precipitated from the liquid phase with silver nitrate solution.

For comparison, the remaining solid is homogenized with water and admixed with acid whereupon the free acid precipitates. The precipitated solid is rapidly redissolved in alkali solution, again precipitated with acid, and dried. The solid is dissolved in potassium hydroxide, and added to cyanide-type silver electrolytes as a basic brightener together with the salt according to the invention.

EXAMPLE 6

In a further reaction, both the liquid phase and the solid phase are stirred up with water, and then the slightly soluble silver salt is precipitated therefrom with silver nitrate.

We claim:

1. A slightly water soluble metal salt having the formula I

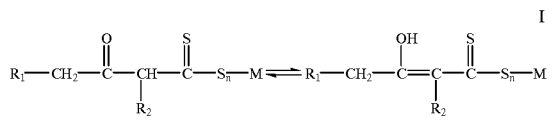

wherein $R_1$ and $R_2$ are the same or different and represent hydrogen or a lower alkyl group of from 1 to 3 carbon atoms, M is the cation of a metal selected from the group consisting of silver, copper, lead, bismuth, antimony, cobalt, iron, zinc, palladium, molybdenum, tin, and gold, and n is 1 or 2, or mixture, thereof.

2. A process for the preparation of a slightly water-soluble metal salt having the formula I

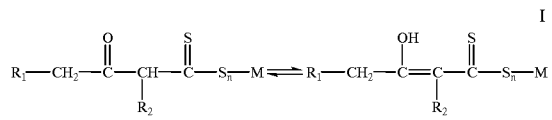

wherein $R_1$ and $R_2$ are the same or different and represent hydrogen or a lower alkyl group of from 1 to 3 carbon atoms, M is the cation of a metal selected from the group consisting of silver, copper, lead, bismuth, antimony, cobalt, iron, zinc, palladium, molybdenum, tin, and gold, and n is 1 or 2, or mixture, thereof, characterized in that carbon disulfide is reacted with a ketone having the formula II

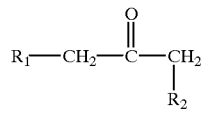

wherein $R_1$ and $R_2$ have the same meaning as above, optionally with the addition of a non-aqueous inert solvent, in the presence of strong alkali, followed by, precipitation of the slightly water-soluble metal salt of formula I by the addition of an aqueous solution of a metal salt of the cation M.

3. The process according to claim 2, wherein the strong alkali is potassium hydroxide.

4. In an electrolytic silver plating bath, the improvement wherein the bath contains as a gloss additive the slightly water-soluble metal salt having the formula I

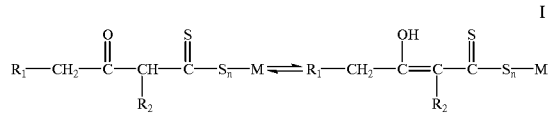

wherein $R_1$ and $R_2$ are the same or different and represent hydrogen or a lower alkyl group of from 1 to 3 carbon atoms, M is the cation of a metal selected from the group consisting of silver, copper, lead, bismuth, antimony, cobalt, iron, zinc, palladium, molybdenum, tin, and gold, and n is 1 or 2, or mixture, thereof.

5. The electrolytic silver plating bath according to claim 4, wherein M is the cation of silver.

* * * * *